United States Patent [19]

Bertagnoli

[11] Patent Number: 5,480,442
[45] Date of Patent: Jan. 2, 1996

[54] FIXEDLY ADJUSTABLE INTERVERTEBRAL PROSTHESIS

[75] Inventor: Rudolf Bertagnoli, Göttingen, Germany

[73] Assignee: MAN Ceramics GmbH, Deggendorf, Germany

[21] Appl. No.: 265,190

[22] Filed: Jun. 24, 1994

[30] Foreign Application Priority Data

Jun. 24, 1993 [DE] Germany ............... 43 20 987.4
May 19, 1994 [DE] Germany ............... 44 17 629.5

[51] Int. Cl.$^6$ ...................................................... A61F 2/44
[52] U.S. Cl. ........................... 623/17; 606/61; 606/63
[58] Field of Search .................. 623/17, 16; 606/61–63, 606/71

[56] References Cited

U.S. PATENT DOCUMENTS

| | | | |
|---|---|---|---|
| 3,426,364 | 2/1969 | Lumb | 623/17 |
| 4,349,921 | 9/1982 | Kuntz | 623/17 |
| 4,401,112 | 8/1983 | Rezaian . | |
| 4,553,273 | 11/1985 | Wu . | |
| 4,759,769 | 7/1988 | Hedman et al. | 623/17 |
| 4,834,757 | 5/1989 | Brantigan | 623/17 |
| 4,932,975 | 6/1990 | Main et al. | 623/17 |
| 5,236,460 | 8/1993 | Barber | 623/17 |
| 5,258,031 | 11/1993 | Salib et al. | 623/17 |
| 5,304,179 | 4/1994 | Wagner | 606/61 |
| 5,306,310 | 4/1994 | Siebels | 623/17 |
| 5,360,430 | 11/1994 | Lin | 606/61 |
| 5,375,823 | 12/1994 | Navas | 267/195 |

FOREIGN PATENT DOCUMENTS

| | | | |
|---|---|---|---|
| 0282161 | 9/1988 | European Pat. Off. . | |
| 3637314 | 5/1988 | Germany . | |
| 3729600 | 3/1989 | Germany . | |
| 9107494 | 10/1991 | Germany . | |
| 1560184 | 7/1988 | U.S.S.R. . | |
| 1243353 | 8/1971 | United Kingdom . | |
| 94004100 | 3/1994 | WIPO | 623/17 |
| 94007441 | 4/1994 | WIPO | 623/17 |

*Primary Examiner*—David Isabella
*Assistant Examiner*—Laura Fossum
*Attorney, Agent, or Firm*—Robert W. Becker

[57] ABSTRACT

An implant for replacing vertebrae has a central load bearing member with a first end and a second end. A first support element is positioned at the first end and a second support element is positioned at the second end. At least one of the first and second support elements has a contact surface, wherein an angle of the contact surface relative to the central load bearing member and the adjacent vertebrae is adjustable for abutting at the adjacently arranged vertebrae. After adjusting the angle of the contact surface, the first and second support elements are fixedly connected to the central load bearing member.

19 Claims, 4 Drawing Sheets

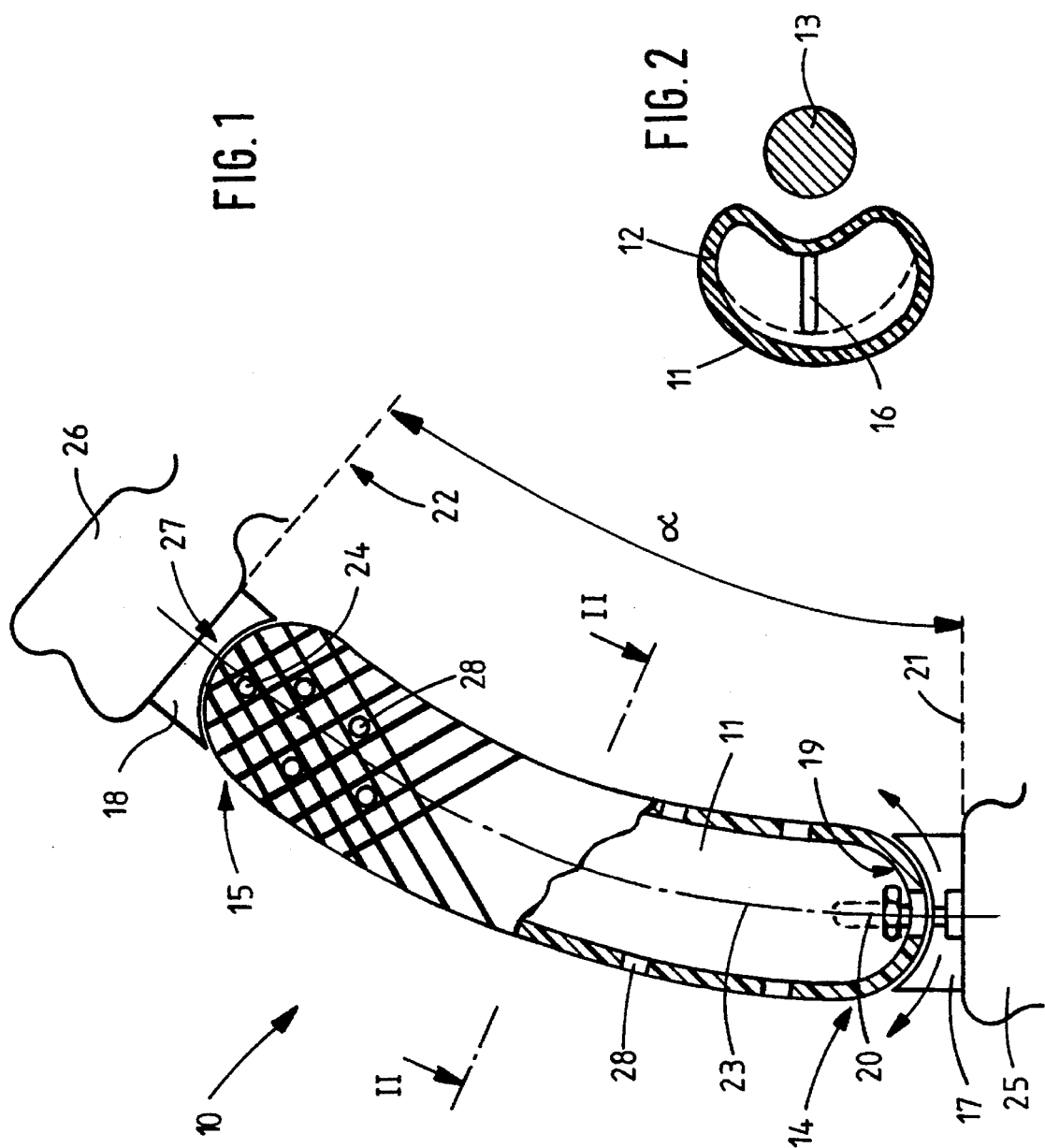

FIXEDLY ADJUSTABLE INTERVERTEBRAL PROSTHESIS

BACKGROUND OF THE INVENTION

The present invention relates to an implant for replacing vertebrae, the implant comprised of a central load bearing member having at either end a support element with a contact surface wherein an angle of the contact surface relative to the load bearing member is adjustable to fit a neighboring vertebra.

When in the human spine individual or multiple bone elements (vertebrae) can no longer fulfill their support function due to the presence of tumors or the action of force, they must be removed surgically and replaced with implants. Suitable implants must take over the mechanical task of supporting the neighboring vertebrae. For this purpose, the replacement elements are inserted between the intact vertebrae and are attached to them.

When a single vertebra must be replaced, it is sufficient to insert an implant that is straight with respect to the spinal axis. However, when it is necessary to replace a plurality of vertebrae, for example, when an expansive tumor has to be removed, the curvature of the spine must be considered for the support implant. Depending on the location within the spine (cervical vertebral column, thorax vertebral column, or lumbar vertebral column) the kyphosis or lordosis must be continued within the implant.

From British patent 1 243 353 an embodiment is known in which the implant is comprised of modular elements which are screwed together and which are fixed relative to one another with a curved splint that is provided with slotted holes such that the assembled vertebral implant corresponds to the desired curvature of the vertebral column. The assembly of the individual elements to form an implant requires time consuming manipulations that must be performed during surgery.

A simple implant is known from German patent 36 37 314 which is comprised of a cylinder-shaped rolled grid element. This known implant, however, must be filled, especially when replacing a plurality of vertebrae, with a bone cement in order to prevent bending of the implant. Ingrowing bone material would not be able to perform the support function because its supporting action would be insufficient.

Another implant is known from U.S. Pat. No. 4,932,975 which comprises a rigid central load bearing member having attached at either end a support element with intermediately positioned elastic members. The elastic members allow for a slanting of the support elements relative to the main axis so that their contact surfaces can be adapted to the angular position of the abutment surfaces of the neighboring vertebrae. The restoring force of the elastic members, however, act continuously as a non-physiological load on the neighboring vertebrae.

The above described disadvantage can be avoided with an implant according to German Gebrauchsmuster 91 07 494 which is comprised of a threaded rod with oppositely oriented threads as a central load bearing member whereby the ends of the threaded rod are screwed into a ball joint which is supported in a support element. The slanted arrangement of the support elements is achieved in this embodiment without spring force. The thread system, however, does not allow for an adaptation to the curvature of the vertebral column.

It is therefore an object of the present invention to provide an implant of the aforementioned kind that can be implanted with simple manipulations and is adaptable without exerting undesirable force loading to the anatomical conditions of the spinal column in order to replace one or more vertebrae.

SUMMARY OF THE INVENTION

An implant for replacing vertebrae according to the present invention is primarily characterized by:
  A central load bearing member having a first end and a second end;
  A first support element positioned at the first end;
  A second support element positioned at the second end;
  At least one of the first and the second support elements having a contact surface wherein an angle of the contact surface relative to the central load bearing member is adjustable for abutting at an adjacently arranged vertebra; and
  Wherein the at least one of the first and second support elements, after adjusting the angle of the contact surface, is fixedly connected to the central load bearing member.

Preferably, the central load bearing member is embodied so as to conform substantially to the curvature of the human spine. The central load bearing member advantageously is a hollow body and the hollow body has a wall comprised of at least one layer.

Expediently, the central load bearing member is in the form of a cylinder. In the preferred embodiment of the present invention, the wall of the load bearing member has perforations. The wall may be in the form of a grate.

Preferably, the first and second support elements comprise a ball joint and are connected with the ball joints to the central load bearing member.

Advantageously, the first and second support elements each comprise a screw for connecting the first and second support elements to the central load bearing member.

In another embodiment of the present invention, the first and second support elements are connected with a connection selected from the group consisting of an adhesive connection, a frictional connection, and a form-fitting connection to the central load bearing member. Preferably, for the connection at least one of the first and second support elements and the central load bearing member is provided with hollow chambers for receiving a material selected from the group consisting of a filler and an adhesive.

Preferably, the central load bearing member and/or the first and second support elements are comprised of fiber-reinforced composite material. Preferably, the fiber-reinforced composite material is a carbon fiber composite material.

In a preferred embodiment of the present invention, the central load bearing member comprises a spreading mechanism for adjusting the axial length of the implant. In the alternative, at least one of the first and second support elements comprises a spreading mechanism for adjusting the axial length of the implant. Preferably, the spreading mechanism comprises a piston for axially displacing the support element.

In another preferred embodiment of the present invention, the central load bearing member is a spreading element for adjusting a length of the implant. The spreading element comprises telescopic members and has a valve for introducing a pressure medium.

The inventive implant is comprised of three components which after adjusting the angle of the contact surface of at least one of the support elements relative to the load bearing member in order to conform to the angle of the vertebra adjacent to it in the implanted state are rigidly connected to one another. The adjustment of the support elements can take place before implanting or when implanted. Such an implant is suitable to replace a plurality of vertebrae and to allow for a satisfactory adaptation to the anatomy of the patient. As a rigid component it provides the required support action without undesirable loads being exerted on the vertebral column.

When using the inventive implant as a replacement for a plurality of adjacently positioned vertebrae, it is advantageous when the load bearing member is curved, especially curved according to the curvature of the vertebral column at the location of surgery.

For realizing the inventive implant various embodiments are possible.

A technically very simple embodiment with respect to manufacturing technologies is comprised of a substantially cylindrical load bearing member which is preferably curved over its length and to which the support elements, with their contact surfaces adjusted to the desired angle, can be connected.

The cross-section of the approximately cylindrical load bearing member is preferably kidney-shaped so that an increased security against damage to the spinal cord is ensured.

The central load bearing member may be in the form of a hollow body that is made of fiber reinforced composite material. By using a winding technique and/or a braiding technique a self-supporting construction may be manufactured which does not require material such as bone cement for increasing the mechanical stability. By using a layering technique, for example, connecting a reticular structure (net) etc. to a tube, is also possible.

The central load bearing member may be embodied so as to be spreadable whereby, for example, screw type spreading mechanisms can be used. According to a further embodiment of the invention the central load bearing member is telescopic and provided with a valve connector via which a pressure medium can be introduced into the hollow chamber for displacing the telescopic members relative to one another. When using a curable pressure medium, for example, bone cement or a resin, the freely movable, respectively, pivotable support elements positioned between the neighboring vertebrae can be automatically aligned during the spreading process relative to the adjacent vertebrae and can be fixed in this position by hardening of the pressure medium. This makes obsolete premeasuring of the angles of the adjacent vertebrae, especially when more than one vertebra must be bridged by the implant.

The inventive implant furthermore allows for a plurality of anchoring possibilities and embodiments for connecting the support elements to the central load bearing member.

According to a simple embodiment of the invention the ends of the load bearing member are concavely or convexly ("dome") shaped to have a semi-spherical contour while the support elements have the matching counter contour. In this manner, the gliding displacement on the dome concave structure of the load bearing member the orientation of the contact surface of one of the support elements can be adjusted continuously so that an orientation may be adjusted in which the contact surfaces of the two support elements have the angle that corresponds to (matches) the angle of the vertebrae neighboring the implant.

It is furthermore possible to employ ball joints whereby each of the support elements has coordinated therewith a ball that is pivotably supported in a cup at the central load bearing member so as to be pivotable in all directions. With screw connections, also in combination with screw caps, different movement and fixation mechanisms can be combined. For example, a selected position of a ball joint can be fixed with a screw cap at the load bearing member.

According to a further inventive embodiment the dome structure of the load bearing member is provided with a slotted opening that for adjusting the correct angle allows for a pivoting movement of the support element together with the screw connected to the support element.

According to another embodiment of the invention an adhesive connection is provided according to which a direct gluing of the support elements on the dome structure of the load bearing member is carried out.

Preferably, a space or hollow chamber for receiving an adhesive material is provided within the load bearing member as well as within the support element for providing the adhesive connection. For a solid load bearing member the dome structure is provided with a bore while within the support element a through opening is provided through which the adhesive material, for example, bone cement, can be introduced after positioning of the support element. A stable form-locking connection is thus achieved.

For this purpose a hollow-core load bearing member is provided at its end with a bore. Within the hollow body an inner closure plate for reducing the filling space is provided. It is also possible not to use a closure plate and to fill the entire hollow chamber with bone material (no support action) so that after ingrowth of bone material a column results. The fixation of the support element with an adhesive material to be introduced into the central load bearing member is ensured especially with an anchoring rod that is fixedly connected to the support element and is surrounded by the adhesive material.

For an implant that is spreadable with a pressure medium the support element may also be provided with an anchoring rod projecting into the interior of the load bearing member which rod extends into the pressure medium, especially a curable medium, and is thus fixed therein. However, other mechanisms are also conceivable, such as a pressure plate, which due to the pressure of an introduced medium (even a non-curable fluid) achieves a frictional connection between the support element and the load bearing member.

With the inventive implant in its various embodiments an optimal adaptation to the anatomical requirements is possible without expensive arresting devices.

The implant is especially suitable to be used in combination with mechanical spreading systems. For a load bearing member with a circular cross-section a double-sided hollow screw with inner or outer counter-directed threads can be used onto which outer threads or into which inner threads the two parts of a transversely divided load bearing member can be screwed. Spreading elements of this kind are known, for example, from U.S. Pat. Nos. 4,553,273 and 4,401,112.

It is also possible that the spreading action does not take place at the load bearing member, but at one of the support elements. In a simple construction a nut with an inner thread is connected to one part of the support element so as to be fixed but rotatable and the second part of the support element is screwed into this nut.

BRIEF DESCRIPTION OF THE DRAWINGS

The object and advantages of the present invention will appear more clearly from the following specification in conjunction with the accompanying drawings, in which:

FIG. 1 shows a first embodiment;

FIG. 2 shows a cross-section of FIG. 1; and

DESCRIPTION OF THE PREFERRED EMBODIMENTS

Figure 4:
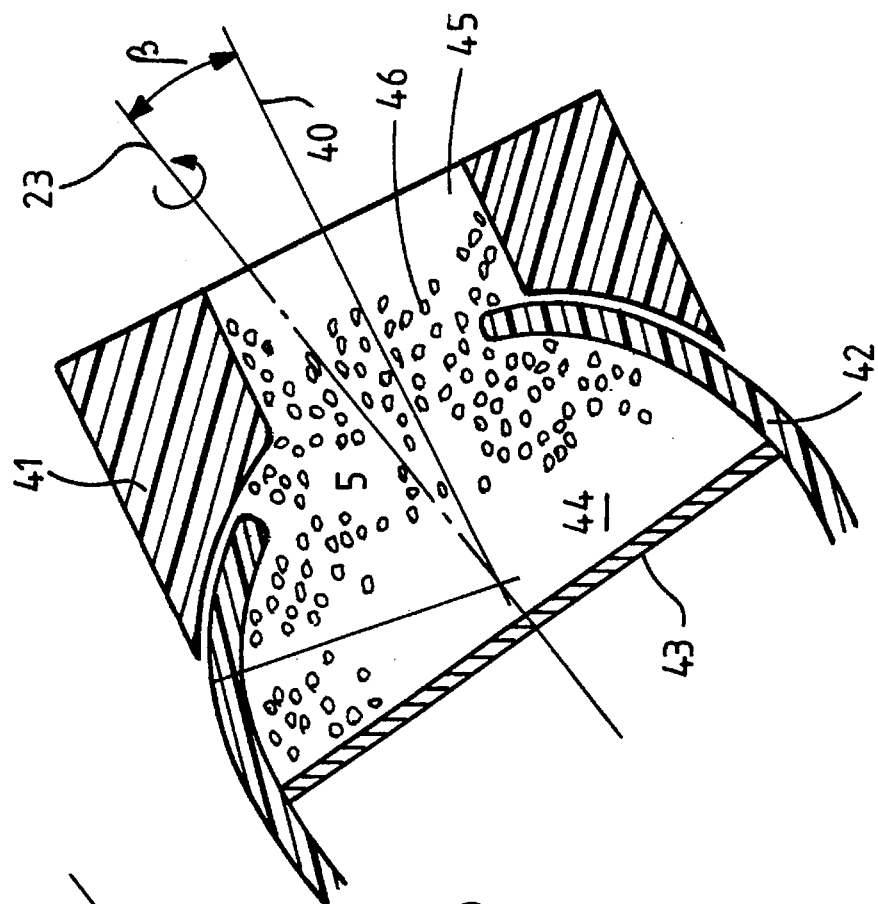
FIGS. 3–9 show further embodiments of the inventive implant.

The present invention will now be described in detail with the aid of several specific embodiments utilizing FIGS. 1 through 9.

FIG. 1 shows a vertebral implant 10 comprised of a central load bearing member 11 made of fiber-reinforced composite material (plastic), for example, reinforced with carbon fibers, which for bridging two or more vertebrae surgically removed from a patient is of an elongate form and bent according to the curvature of the vertebral column.

As shown in FIG. 2, the cross-section 12 of the load bearing member 11 is kidney-shaped in order to ensure a sufficient distance to the spinal cord 13.

The ends, respectively, domes 14 and 15 of the load bearing member 11 are semi-spherical and are provided with a slotted hole 16 (FIG. 2) for fixing therein a support element 17, respectively, 18. The support elements 17, 18 are provided with semi-spherical recesses 19 and 24 on their ends facing the load bearing member 11. With a screw 20 the support element 17 is fixedly connected to the load bearing member 11. The support element 17, 18 are pivotable in the direction of the shown arrows, i.e., parallel to the slotted holes 16 about the center of the dome so that the orientation (angular position or angle) of the contact surfaces 21, 22 of the support element 17, 18 can be adapted to (matched with) the angle of the adjacently arranged vertebrae 25, 26 of the patient.

Figure 3:
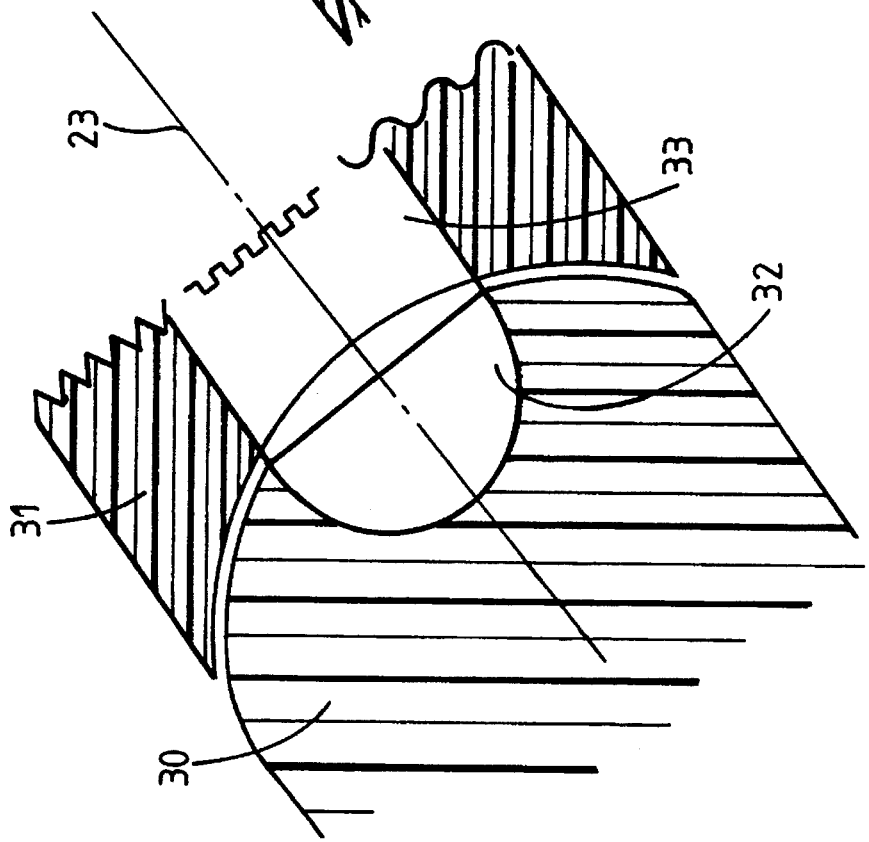

The central load bearing member 30 may be in the form of a hollow body (FIG. 1) or in the form of a solid component as shown, for example, in FIG. 3. For the construction of the load bearing member homogenous as well as layered structures are possible.

Figure 5A:
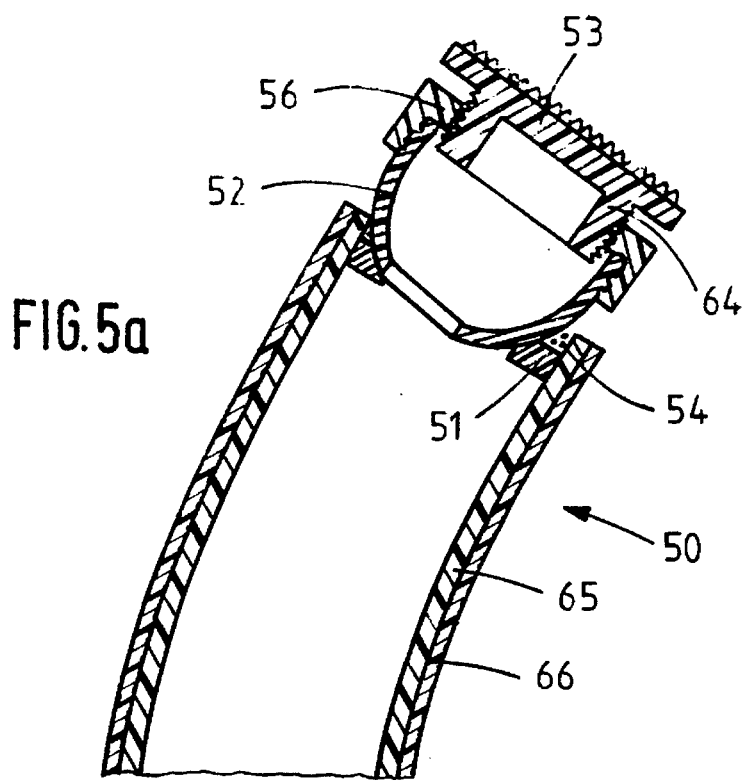

FIGS. 3, 4 and 5a show the load bearing members 30, 42, 57 of a homogenous structure. The load bearing member 50 according to FIG. 5a in contrast is made of two layers, for example, from a tube 65 and a net-like outer layer 66.

FIG. 3 shows a variant in which the support element 31 is directly glued to the dome of the load bearing member 30. For increasing the form-locking action, the load bearing member 30 and the support element 31 can be provided with communicating hollow chambers 32 and 33 which are filled with an adhesive material, for example, bone cement or bone material.

In general, the axis 40 of the support element 41 is rotated about an angle β relative to the axis 23 of the load bearing member (shown in FIG. 4 in connection with a load bearing member 42 in the form of a hollow body). In order to reduce the amount of adhesive material within the dome area of the load bearing member 42 an internal closure plate 43 is provided. After positioning the support element 41 at the selected angle β the hollow chamber 44 remaining within the dome of the load bearing member and the opening 45 of the support element 41 are filled with adhesive material 46 that is hardened before or after implantation.

The hollow body 42, however, may also be completely filled with bone material so that a bone column results after bone material has grown in. A support function is not provided by this bone column.

Figure 5B:
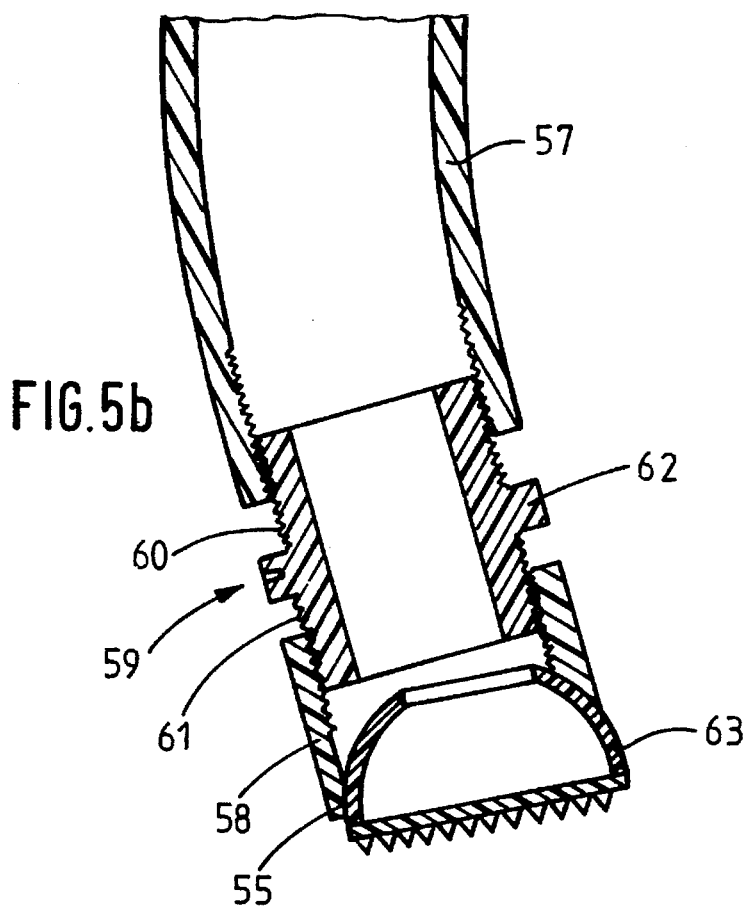

A reversal of the spherical surfaces at the dome of the main load bearing member and the support elements is also possible: The end of the load bearing member is concave and the support elements at their ends facing the load bearing member are convex. Embodiments in connection with a tubular load bearing member are shown in FIGS. 5a and 5b.

According to FIG. 5a a support ring 51 is provided at the load bearing member 50 the inner wall of which is spherically shaped in order to receive the semi-spherical part 52 of the support element 53. The inner wall of the support ring 51 is coated with an adhesive material in order to fix the support element 52, 53 in its position after adjustment of the desired angle. An annular gap 54 at the end of the load bearing member 50 is filled with an adhesive material for increasing the adhesive connection. Instead of the support ring 51 a spherically shaped edge 55 of the load bearing member 58 (FIG. 5b) can serve as a support for the support element 63.

With a solid load bearing member the support element is glued to a semi-spherical recess at the end of the load bearing member.

It is furthermore advantageous when the implant is provided with a spreading mechanism. An example for a particular realization is shown in FIGS. 5a and 5b.

In FIG. 5a an embodiment is shown in which the support element is comprised of a semi-spherical part 52 and a support plate 53 which parts are connected to one another with a nut 56. The nut 56 is connected to the semi-spherical part 52 so as to be axially form-locking and circumferentially rotatable. At the free end the nut 56 has an inner thread for receiving a socket 64 of the support plate 53, the socket 64 having an outer thread. By rotating the nut 56 the support plate 53 is axially displaceable. This spreading mechanism can be connected to only one of the support elements.

According to FIG. 5b the spreading action is carried out at the load bearing member 57. For this purpose, the load bearing member 57 is divided into two parts 57 and 58 that are connected with one another with a two sided hollow screw 59. The screw 59 has two counter-oriented threads 60 and 61 and a central ring 62 which has a polygonal circumference or bores for receiving a tool with which the screw 59 in the implanted state can be rotated in order to spread the implant. The support element 63 in this case form a unitary part with the main load bearing member 58, i.e., are rigidly connected thereto.

Figure 6:
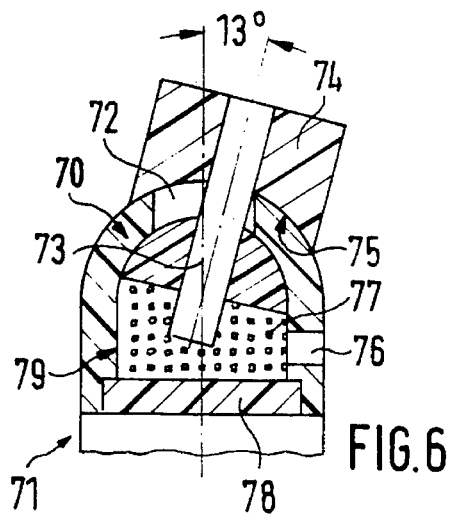

FIG. 6 shows a convexly shaped dome 70 of a load bearing member 71 that is provided with a central bore 72 through which an anchoring rod 73 of the support element 74 extends into a hollow chamber 57 of the load bearing member 71. The support element 74 can be pivoted due to its convex connecting surface 75 and the oversized bore 72 in all directions by about 26°. Via an opening 76 a curable medium 77 is introduced into the hollow chamber 75 of the load carrying member 71 which after curing fixes the anchoring rod in the desired position. In order to limit the required amount of curable fixation medium 77, the hollow chamber 75 is separated from the interior of the load bearing member 71 with a closure plate 78 positioned in the vicinity of the dome 70.

Figure 7:
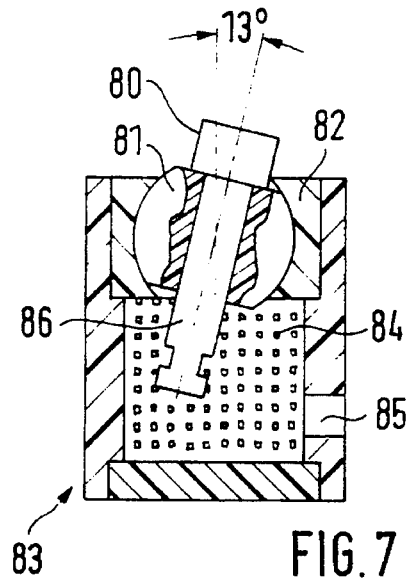

FIG. 7 shows an embodiment in which the support element 80 is rotatably and pivotably connected with the load bearing member 83 via a ball joint 81, 82. In this case, the anchoring is carried out with an adhesive 84 which is introduced through opening 85 in the wall of the load bearing member 83 for fixing the anchoring rod 86 in its surroundings. Short implants, in general, are only provided with one movable, respectively, adjustable support element whereby the second support element is rigidly connected to the load bearing member or is directly formed by the other end of the main load bearing member.

Figure 9:
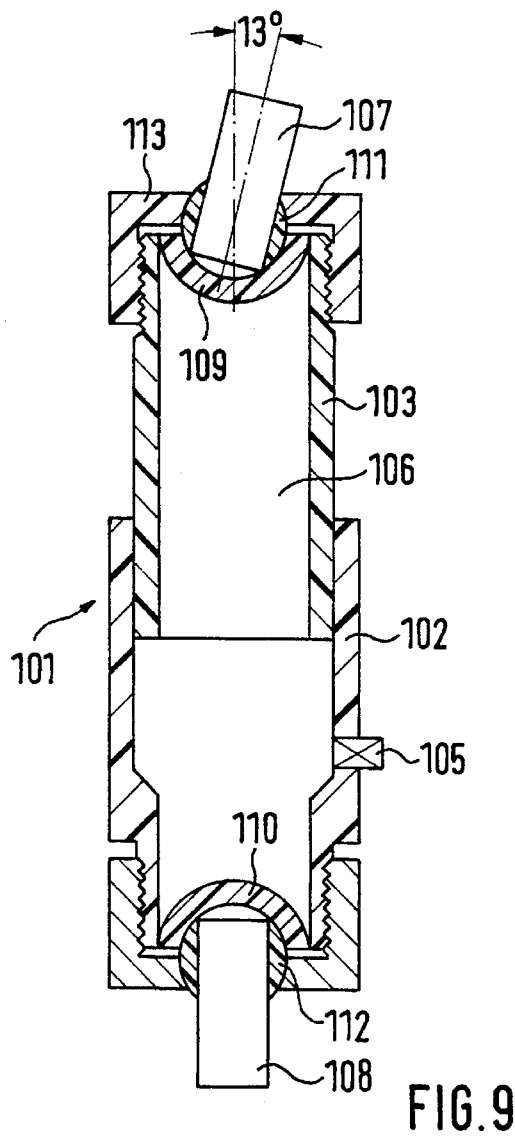
Figure 8:
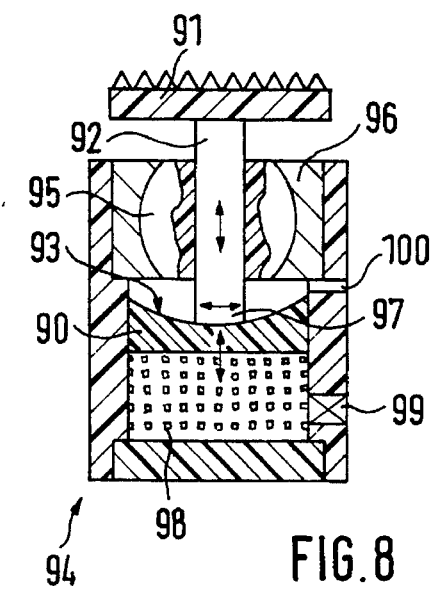

FIGS. 8 and 9 show embodiments in which the support element, respectively, the load bearing member are in the form of spreading elements.

According to FIG. 8 the support element 91 having a piston 90 is the spreading element. The plate-shaped support element 91 is supported via the anchoring rod 92 at the concave surface 93 of the piston 90 and is thus pivotably supported within the load bearing member. For this purpose, the anchoring rod 92 is fixedly connected to the ball 95 of a ball joint (95, 96) which is rotatably and pivotably supported in the annular cup 96 that is connected to the load bearing member 94 so that the support element 91 in the implanted state can be aligned with the neighboring vertebrae. For this alignment, the free end 97 of the anchoring rod 92 glides on the concave surface 93 of the piston 90. By introducing a pressure medium 98 through the valve 99 of the load bearing member 94, the piston 90 is forced toward the dome of the load bearing member so that the force is transmitted via the anchoring rod 92 onto the support element 91. Via a further opening 100 a curable medium can be introduced to the concave side 93 of the piston 90 for fixing the anchoring rod 92. In the embodiment according to FIG. 8 it is sufficient when only one support element 91 is axially displaceable.

According to FIG. 9 the load bearing member 101 is in the form of a spreading element comprised of two telescopic tubes 102, 103. Via a valve 105 a pressure medium, which may be a gas, a liquid or a curable medium such as bone cement, can be introduced under pressure, and the implant can thus be spread via the support element toward the adjacently arranged vertebrae.

In this embodiment the two ends of the implant are moved. The pressure within the interior 106 of the load bearing member 101 can simultaneously be used for frictional connection of the support elements 107, 108 such that, for example, the cups 109, 110 of the ball joints 111, 112 are forced with their specially designed frictional surface against the balls of the ball joints 111, 112.

It will not always be necessary to make both support elements pivotable. However, when replacing larger vertebrae, vertebrae in the vicinity of the lumbar vertebral column, or a plurality of vertebrae, a pivotability on both ends of the implant is more expedient with respect to the anatomy of the vertebral column.

The present invention is, of course, in no way restricted to the specific disclosure of the specification and drawings, but also encompasses any modifications within the scope of the appended claims.

What I claim is:

1. A vertebral implant for replacing vertebrae, said implant comprising:

a central load bearing member configured and arranged to be inserted between adjacent vertebra having a first and second end;

a first support element positioned at said first end;

a second support element positioned at said second end;

at least one of said first and second support elements having a contact surface for abutting an adjacently arranged vertebra;

at least one of said first and second support elements further having universal adjustment means for allowing an angle of said contact surface relative to said central load bearing member to be universally adjusted; and at least one of said first and second support elements having means for fixedly connecting said universal adjustment means to said central load bearing member after adjusting said angle.

2. An implant according to claim 1, wherein:

said central load bearing member is configured so as to conform substantially to a curvature of a human spine;

said central load bearing member is a hollow body; and said hollow body has a wall including at least one layer.

3. An implant according to claim 2, wherein said central load bearing member is in a form of a cylinder.

4. An implant according to claim 2, wherein said wall has perforations.

5. An implant according to claim 2, wherein said wall is in a form of a grate.

6. An implant according to claim 1, wherein said universal adjustment means comprises a ball joint.

7. An implant according to claim 1, wherein said means for fixedly connecting said universal adjustment means to said central load bearing member is selected from the group consisting of an adhesive connection, a frictional connection, and a form-fitting connection.

8. An implant according to claim 7, wherein said means for fixedly connecting said universal adjustment means to said central load bearing member comprises providing at least one of said first and second support elements and said central load bearing member with hollow chambers for receiving a material selected from the group consisting of a filler and an adhesive.

9. An implant according to claim 1, wherein said central load bearing member comprises fiber-reinforced composite material.

10. An implant according to claim 9, wherein said fiber-reinforced composite material is a carbon fiber composite material.

11. An implant according to claim 1, wherein said first and second support elements comprise fiber-reinforced composite material.

12. An implant according to claim 11, wherein said fiber-reinforced composite material is a carbon fiber composite material.

13. An implant according to claim 1, wherein said central load bearing member and said first and second support elements comprise fiber-reinforced composite material.

14. An implant according to claim 13, wherein said fiber-reinforced composite material is a carbon fiber composite material.

15. An implant according to claim 1, wherein said central load bearing member comprises a spreading mechanism for adjusting an axial length of said implant.

16. An implant according to claim 1, wherein at least one of said first and second support elements comprises a spreading mechanism for adjusting an axial length of said implant.

17. An implant according to claim 16, wherein said spreading mechanism comprises a piston for axially displacing said support element.

18. An implant according to claim 1, wherein said central load bearing member is a spreading element for adjusting a length of said implant.

19. An implant according to claim 18, wherein said spreading element comprises telescopic members and has a valve for introducing a pressure medium.

* * * * *